(12) United States Patent
Chopra et al.

(10) Patent No.: US 9,006,427 B2
(45) Date of Patent: *Apr. 14, 2015

(54) PHOTOCHROMIC MATERIALS DEMONSTRATING IMPROVED FADE RATES

(71) Applicant: Transitions Optical, Inc., Pinellas Park, FL (US)

(72) Inventors: Anu Chopra, Pittsburgh, PA (US); Patrick M. Brown, Moon Township, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,898

(22) Filed: Feb. 7, 2014

(65) Prior Publication Data

US 2014/0155598 A1 Jun. 5, 2014

Related U.S. Application Data

(63) Continuation of application No. 11/860,682, filed on Sep. 25, 2007, now Pat. No. 8,748,634.

(60) Provisional application No. 60/855,270, filed on Oct. 30, 2006.

(51) Int. Cl.
*C07D 413/10* (2006.01)
*C07D 311/94* (2006.01)
*C09K 9/02* (2006.01)
*G02B 5/23* (2006.01)
*G03C 1/73* (2006.01)

(52) U.S. Cl.
CPC ............. *C07D 413/10* (2013.01); *C09K 9/02* (2013.01); *C09K 2211/145* (2013.01); *G02B 5/23* (2013.01); *G03C 1/73* (2013.01); *C07D 311/94* (2013.01)

(58) Field of Classification Search
CPC ........................... C07D 413/10; C07D 311/94
USPC .......................................................... 549/382
See application file for complete search history.

(56) References Cited

U.S. PATENT DOCUMENTS 8,748,634 B2 * 6/2014 Chopra et al. ................ 549/382

* cited by examiner

*Primary Examiner* — Yong Chu
(74) *Attorney, Agent, or Firm* — The Webb Law Firm

(57) ABSTRACT

Various photochromic materials are provided that are essentially free of polymerizable unsaturated groups, and comprise:
a) an indeno[2',3':3,4]naphtho[1,2-b]pyran; and
b) an electron-withdrawing, non-conjugating group bonded at the 11-position of the indeno[2',3':3,4]naphtho[1,2-b]pyran.

Alternative embodiments include various substituents at other positions of the indeno[2',3':3,4]naphtho[1,2-b]pyran.

2 Claims, No Drawings

# PHOTOCHROMIC MATERIALS DEMONSTRATING IMPROVED FADE RATES

CROSS-REFERENCE TO RELATED APPLICATIONS

This application is a continuation of U.S. application Ser. No. 11/860,682, filed Sep. 25, 2007, now U.S. Pat. No. 8,748,634 B2, which claims priority from U.S. Provisional Patent Application No. 60/855,270 filed Oct. 30, 2006, each of which is incorporated herein by reference in its entirety.

FIELD OF THE INVENTION

The present invention generally relates to photochromic materials, and more particularly relates to photochromic materials comprising an indeno[2',3':3,4]naphtho[1,2-b]pyran demonstrating improved fade rates. The present invention further relates to photochromic articles that comprise such photochromic materials.

BACKGROUND OF THE INVENTION

Photochromic materials undergo a structural transformation from one form (or state) to another in response to certain wavelengths of electromagnetic radiation, with each form having a characteristic absorption spectrum for visible radiation. For example, thermally reversible photochromic materials are capable of transforming from a ground-state form to an activated-state form in response to actinic radiation, and reverting back to the ground-state form in response to thermal energy and in the absence of the actinic radiation. As used herein, the term "actinic radiation" refers to electromagnetic radiation that is capable of causing a photochromic material to transform from one form or state to another.

Photochromic materials adapted for use in ophthalmic applications are usually essentially colorless or "optically clear" when not exposed to actinic radiation (i.e., in the ground-state form) and exhibit a visible color that is characteristic of the absorption spectrum of the activated-state form of the photochromic material upon exposure to actinic radiation. Photochromic compositions and articles that contain one or more photochromic materials, for example, photochromic lenses for eyewear applications, may display clear and colored states that generally correspond to the optically clear and colored states of the photochromic material(s) that they contain.

For certain applications, it is desirable that the photochromic material be able to make the transition from the colorless, ground-state form to the colored, activated-state form as quickly as possible. It is often additionally desirable that the photochromic material be able to make the reverse transition from the colored, activated-state form back to the colorless, ground-state form as quickly as possible. For example, in photochromic eyewear applications, ophthalmic lenses comprising photochromic materials may transform from a clear state to a colored state as the wearer moves from a region of low actinic radiation, such as, indoors, to a region of high actinic radiation, such as, exposed to sunlight. As the lenses become colored, less electromagnetic radiation having wavelengths within the visible and/or ultraviolet regions of the electromagnetic spectrum is transmitted through the lens to the wearer's eyes. In other words, more electromagnetic radiation is absorbed by the lenses in the colored state than in the clear state. When the wearer subsequently moves from the region of high actinic radiation back to a region of low actinic radiation, the photochromic material in the eyewear may revert from the colored, activated-state form to the optically clear, ground-state form in the absence of actinic radiation and absorbance of thermal energy. If the transition from the optically clear state to the colored state takes several minutes or more upon exposure to actinic radiation, the benefit of the reduced transmittance of visible and/or ultraviolet radiation that may be derived from the lenses in the colored state may be diminished. Further, if the transition from the colored state to the optically clear state takes several minutes or more once removed from actinic radiation, the wearer's vision may be less than optimal during this time due to the combined effects of the lower ambient light and the reduced transmission of visible light through the colored lenses. Accordingly, it would be desirable to develop photochromic materials that may more quickly transition from the optically clear, ground-state form to the colored, activated-state form, as well as from the colored, activated-state form to the optically clear, ground-state form.

Additionally, conventional photochromic materials often exhibit a "directional" dependency. That is, color change is most pronounced when the photochromic material is facing a light source directly, such as direct sunlight, with the photochromic effect being less noticeable or complete when the material is exposed indirectly to a light source. Accordingly, there is a need for photochromic materials that are less directionally dependent, demonstrating a more consistent degree of color change substantially independently of the orientation of the light source relative to the photochromic material.

SUMMARY OF THE INVENTION

In accordance with the present invention, photochromic materials that are essentially free of polymerizable unsaturated groups are provided. The photochromic materials comprise:
 a) an indeno[2',3':3,4]naphtho[1,2-b]pyran;
 b) an electron-withdrawing, non-conjugating group bonded at the 11-position of the indeno[2',3':3,4]naphtho[1,2-b]pyran; and
 c) two groups bonded at the 13-position of the indeno[2',3':3,4]naphtho([1,2-b]pyran, provided that said groups do not combine to form a spirocyclic group.

The present invention further provides photochromic materials that are essentially free of polymerizable unsaturated groups, comprising:
 a) an indeno[2',3':3,4]naphtho[1,2-b]pyran;
 b) an electron-withdrawing, non-conjugating group bonded at the 11-position of the indeno[2',3':3,4]naphtho[1,2-b]pyran; and
 c) moderate to strong electron-donating groups bonded at each of the 6- and 7-positions of the indeno[2',3':3,4]naphtho[1,2-b]pyran.

Additionally, the present invention provides a photochromic article comprising:
 (a) a substrate; and
 (b) any of the photochromic materials above, wherein the photochromic materials are in contact with at least a portion of the substrate.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The various embodiments and examples of the present invention as presented herein are each understood to be non-limiting with respect to the scope of the invention.

As used in the following description and claims, the following terms have the indicated meanings:

The terms "on", "appended to", "affixed to", "bonded to", "adhered to", or terms of like import means that the designated item, e.g., a coating, film or layer, is either directly connected to (e.g., superimposed on) the object surface, or indirectly connected to the object surface, e.g., through one or more other coatings, films or layers.

The term "ophthalmic" refers to elements and devices that are associated with the eye and vision, such as but not limited to, lenses for eyewear, e.g., corrective and non-corrective lenses, and magnifying lenses.

The term "optical quality", as used for example in connection with polymeric materials, e.g., a "resin of optical quality" or "organic polymeric material of optical quality" means that the indicated material, e.g., a polymeric material, resin, or resin composition, is or forms a substrate, layer, film or coating that can be used as an optical article, such as an ophthalmic lens, or in combination with an optical article.

The term "rigid", as used for example in connection with an optical substrate, means that the specified item is self-supporting.

The term "light influencing function", "light influencing property" or terms of like import means that the indicated material, e.g., coating, film, substrate, etc., is capable of modifying by absorption (or filtering) of incident light radiation, e.g., visible, ultraviolet (UV) and/or infrared (IR) radiation that impinges on the material. In alternate embodiments, the light influencing function can be light polarization, e.g., by means of a polarizer and/or dichroic dye; a change in light absorption properties, e.g., by use of a chromophore that changes color upon exposure to actinic radiation, such as a photochromic material; transmission of only a portion of the incident light radiation, e.g., by use of a fixed tint such as a conventional dye; or by a combination of one or more of such light influencing functions.

The term "adapted to possess at least one light influencing property", as used for example in connection with a rigid optical substrate, means that the specified item is capable of having the light influencing property incorporated into or appended to it. For example, a plastic matrix that is adapted to possess a light influencing property means that the plastic matrix has sufficient internal free volume to accommodate internally a photochromic dye or tint. The surface of such a plastic matrix may alternatively be capable of having a photochromic or tinted layer, film or coating appended to it, and/or is capable of having a polarizing film appended to it.

The term "optical substrate" means that the specified substrate exhibits a light transmission value (transmits incident light) of at least 4 percent and exhibits a haze value of less than 1 percent, e.g., less than 0.5 percent, when measured at 550 nanometers by, for example, a Haze Gard Plus Instrument. Optical substrates include, but are not limited to, optical articles such as lenses, optical layers, e.g., optical resin layers, optical films and optical coatings, and optical substrates having a light influencing property.

The term "transparent", as used for example in connection with a substrate, film, material and/or coating, means that the indicated substrate, coating, film and/or material has the property of transmitting light without appreciable scattering so that objects lying beyond are entirely visible.

The phrase "an at least partial film" means an amount of film covering at least a portion, up to the complete surface of the substrate. As used herein, a "film" may be formed by a sheeting type of material or a coating type of material. For example, a film may be an at least partially cured polymeric sheet or an at least partially cured polymeric coating of the material indicated. The phrase "at least partially cured" means a material in which from some to all of the curable or cross-linkable components are cured, crosslinked and/or reacted.

The term "photochromic" means having an absorption spectrum for at least visible radiation that varies in response to at least actinic radiation. As used herein, the term "photochromic material" means any substance that is adapted to display photochromic properties, i.e. adapted to have an absorption spectrum for at least visible radiation that varies in response to at least actinic radiation. As discussed above, as used herein, the term "actinic radiation" refers to electromagnetic radiation that is capable of causing a photochromic material to transform from one form or state to another.

Examples of photochromic materials include, without limitation, photochromic groups (e.g., indeno-fused naphthopyrans, etc.), as well as polymers, oligomers, monomers, and other compounds that comprise at least one photochromic group. As used herein, the term "group" means an arrangement of one or more atoms. Further, as used herein, the term "photochromic group" refers to an arrangement of atoms comprising a photochromic moiety. The term "moiety", as used herein, means a part or portion of an organic molecule that has a characteristic chemical property. As used herein, the term "photochromic moiety" refers to the portion of a photochromic group that can undergo reversible transformation from one state to another upon exposure to actinic radiation.

The photochromic materials according to various non-limiting embodiments disclosed herein may comprise, in addition to a photochromic group, one or more other groups (e.g., functional groups, aliphatic groups, alicyclic groups, aromatic groups, heteroaromatic groups, heterocyclic groups, etc.) that are linked or fused to the photochromic group or another portion of the photochromic material. As used herein, the term "linked" means covalently bonded. Further, as used herein, the term "fused" means covalently bonded in at least two adjacent positions.

The term "indeno[2',3':3,4]naphtho[1,2-b]pyran" refers to a photochromic group that may be represented by the general structure (i) (below), and which comprises one or more group(s) bonded to the pyran ring at an available position adjacent to the oxygen atom (i.e., indicated as the groups B and B' bonded at the 3-position in structure (i) below), which may aid in stabilizing the open-form of the indeno-fused naphthopyran. Non-limiting examples of groups that may be bonded to the pyran ring are described in more detail herein below with reference to the groups B and B'. As used herein, terms such as "13-position," "11-position," "6-position," etc. refer to the 13-, 11-, 6-positions, etc. (respectively) of the ring atoms of the indeno-fused naphthopyran as shown in structure (i).

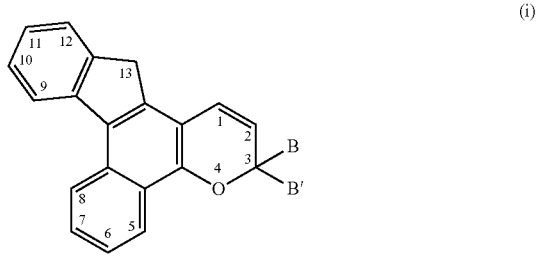

(i)

Further, it will be appreciated by those skilled in the art that any available position in the structure (i) may be substituted or unsubstituted as required. Non-limiting examples of groups that may be bonded to available positions on the indeno[2',3':3,4]naphtho[1,2-b]pyran according to various non-limiting embodiments disclose herein are set forth herein below in detail.

Moreover, it should be appreciated that where listings of possible substituent groups are provided herein using headings or sub-heading (e.g., (a), (b) . . . ; (1), (2) . . . ; (i) (ii) . . . ; etc), these headings or subheadings are provided only for convenience of reading and are not intended to limit the choice of substituents groups.

According to the present invention, a photochromic material that is essentially free of polymerizable unsaturated groups is provided. The photochromic material comprises:
  a) an indeno[2',3':3,4]naphtho[1,2-b]pyran;
  b) an electron-withdrawing, non-conjugating group bonded at the 11-position of the indeno[2',3':3,4]naphtho[1,2-b]pyran; and
  c) two groups bonded at the 13-position of the indeno[2',3':3,4]naphtho[1,2-b]pyran, provided that said groups do not combine to form a spirocyclic group.

By "polymerizable unsaturated groups" is meant functional groups containing double or triple bonds that are capable of participating in an addition polymerization reaction. Such groups may include, for example, alkynyl, vinyl, acrylic, methacrylic, and allylic groups. By "essentially free of" polymerizable unsaturated groups is meant that there are no polymerizable unsaturated groups present on the compound.

The indeno[2',3':3,4]naphtho[1,2-b]pyran of a) may have the structure shown in (i) above and may comprise various substituents as described in more detail below.

The electron-withdrawing, non-conjugating group of b) typically comprises an α-haloalkyl, α,α-dihaloalkyl, trihalomethyl group such as trifluoromethyl, a perhaloalkyl group such as perfluoroethyl, a perhaloalkoxy group such as perfluoropropoxy or perfluoromethoxy, or the substituent group —O—C(O)—R, wherein R is a linear or branched group chosen from a $C_1$-$C_{10}$ alkyl, to form a substituent group such as an acetoxy group, a $C_1$-$C_{10}$ haloalkyl, to form a substituent group such as a 1,1-difluoropropylcarbonyloxy, or a $C_1$-$C_{10}$ perhaloalkyl, to form a substituent group such as a trifluoromethylcarbonyloxy. In one non-limiting embodiment, the electron-withdrawing, non-conjugating group of b) can be a trifluoromethyl group.

The two groups bonded at the 13-position of the indeno[2',3':3,4]naphtho[1,2-b]pyran are non-spirocyclic; i.e., they do not come together to form a spiro ring. They may each be selected from the group consisting of:
  (i) hydrogen, hydroxy, $C_1$-$C_6$ alkyl, hydroxy($C_1$-$C_6$)alkyl, amino, mono- or di-substituted amino, $C_3$-$C_7$ cycloalkyl, allyl, benzyl, mono-substituted benzyl, chloro, fluoro, the group —C(O)W', wherein W' is hydroxy, $C_1$-$C_6$ alkyl, $C_1$-$C_6$ alkoxy, phenyl, mono-substituted phenyl, amino, mono($C_1$-$C_6$)alkylamino or di($C_1$-$C_6$)alkylamino, e.g. N,N-dimethyl amino, N-methyl-N-propyl amino, etc., morpholino, piperidino or pyrrolidyl, said amino substituents being selected from the group consisting of $C_1$-$C_6$ alkyl, phenyl, benzyl and naphthyl, and said benzyl and phenyl substituents being $C_1$-$C_6$ alkyl or $C_1$-$C_6$ alkoxy;
  (ii) the unsubstituted, mono- di- or trisubstituted groups phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, said group substituents in this section (ii) being selected from the group consisting of chloro, fluoro, $C_1$-$C_6$ alkyl, hydroxy($C_1$-$C_6$)alkyl, $C_1$-$C_6$ alkoxy and hydroxy($C_1$-$C_6$)alkoxy;
  (iii) monosubstituted phenyl having a substituent at the para position that is a linking group, —$(CH_2)_t$— or —O—$(CH_2)_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;
  (iv) the group, —$OR^{1'}$, wherein $R^{1'}$, is $C_1$-$C_6$ alkyl, $C_1$-$C_6$ acyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, benzoyl, monosubstituted benzoyl, naphthoyl or monosubstituted naphthoyl, said benzoyl and naphthoyl group substituents being $C_1$-$C_6$ alkyl or $C_1$-$C_6$ alkoxy, or $R^{1'}$ is the group, —$CH(R^{2'})Q$, wherein $R^{2'}$ is hydrogen or $C_1$-$C_3$ alkyl and Q is —CN, —$CF_3$, or —$COOR^{3'}$, wherein $R^{3'}$ is hydrogen or $C_1$-$C_3$ alkyl, or $R^{1'}$ is the group, —C(O)V', wherein V' is hydrogen, $C_1$-$C_6$ alkoxy, phenoxy, mono- or di-($C_1$-$C_6$)alkyl substituted phenoxy, mono- or di-($C_1$-$C_6$)alkoxy substituted phenoxy, the unsubstituted, mono- or di-substituted aryl groups, phenyl and naphthyl, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, said aryl group substituents being $C_1$-$C_6$ alkyl or $C_1$-$C_6$ alkoxy;
  (v) the group —$CH(Q')_2$ wherein Q' is —CN or —$COOR^{4'}$, wherein $R^{4'}$ is hydrogen, $C_1$-$C_6$ alkyl, phenyl($C_1$-$C_3$) alkyl, mono($C_1$-$C_6$)alkyl substituted phenyl($C_1$-$C_3$) alkyl, mono($C_1$-$C_6$)alkoxy substituted phenyl($C_1$-$C_3$) alkyl, or the unsubstituted, mono- or di-substituted aryl groups phenyl or naphthyl, said aryl group substituents being $C_1$-$C_6$ alkyl or $C_1$-$C_6$ alkoxy;
  (vi) the group —$CH(R^{5'})G'$, wherein $R^{5'}$ is hydrogen, $C_1$-$C_6$ alkyl or the unsubstituted, mono- or di-substituted aryl groups phenyl and naphthyl, and G' is —$COOR^{4'}$, —$C(O)R^{5'}$ or —$CH_2OR^{7'}$, wherein $R^{6'}$ is hydrogen, $C_1$-$C_6$ alkyl, the unsubstituted, mono- or di-substituted aryl groups phenyl or naphthyl, amino, mono($C_1$-$C_6$)

alkylamino, di($C_1$-$C_6$)alkylamino, e.g., dimethyl amino, methyl propyl amino, etc., phenylamino, mono- or di-($C_1$-$C_6$)alkyl substituted phenylamino, mono- or di($C_1$-$C_6$)alkoxy substituted phenylamino, diphenylamino, mono- or di($C_1$-$C_6$)alkyl substituted diphenylamino, i.e., each phenyl has one or two $C_1$-$C_6$ alkyl substituents, mono- or di($C_1$-$C_6$)alkoxy substituted diphenylamino, i.e., each phenyl has one or two $C_1$-$C_6$ alkoxy substituents, morpholino, or piperidino, wherein $R^{7'}$ is hydrogen, —C(O)$R_{11}$, $C_1$-$C_6$ alkyl, $C_1$-$C_3$ alkoxy($C_1$-$C_6$) alkyl, phenyl($C_1$-$C_3$)alkyl, mono($C_1$-$C_6$)alkoxy substituted phenyl($C_1$-$C_3$)alkyl, or unsubstituted, mono- or di-substituted aryl groups including phenyl and naphthyl; wherein $R_{11}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, or the unsubstituted, mono- or di-substituted aryl groups including phenyl or naphthyl, each of said aryl group substituents being $C_1$-$C_6$ alkyl or $C_1$-$C_6$ alkoxy; and (vii) the polyalkoxylated group T represented by the formula:

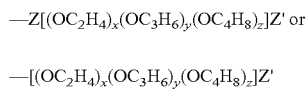

wherein —Z is —C(O)— or —$CH_2$— and Z' is hydroxy, epoxy or $C_1$-$C_3$ alkoxy; with the proviso that the two groups at the 13 position do not combine to form a spirocyclic group.

The group, —($OC_2H_4$)$_x$—, represents poly(ethylene oxide); —($OC_3H_6$)$_y$—, represents poly(propylene oxide); and, —($OC_4H_8$)$_z$—, represents poly(butylene oxide). When used in combination, the poly(ethylene oxide), poly(propylene oxide) and poly(butylene oxide) groups of T may be in a random or block order within the T moiety. The letters x, y and z are each a number between 0 and 50 and the sum of x, y and z is between 2 and 50. The sum of x, y and z may be any number that falls within the range of 2 to 50, e.g., 2, 3, 4 . . . 50. This sum may also range from any lower number to any higher number within the range of 2 to 50, e.g., 6 to 50, 31 to 50. The numbers for x, y, and z are average values and are not necessarily whole numbers, e.g., 9.5 is acceptable.

The groups bonded at the 13-position of the indeno[2',3': 3,4]naphtho[1,2-b]pyran typically independently comprise a $C_1$-$C_6$ alkyl or alkoxy group, hydroxy($C_1$-$C_6$)alkyl, or the polyalkoxylated group T represented by the formula:

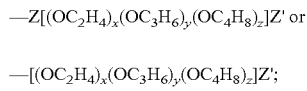

wherein —Z is —C(O)— or —$CH_2$— and Z' is hydroxy, epoxy or $C_1$-$C_3$ alkoxy. Often the groups comprise two methyl groups or one ethyl and one methoxy group.

The present invention further provides photochromic materials that are essentially free of polymerizable unsaturated groups, wherein the photochromic materials comprise:
a) an indeno[2',3':3,4]naphtho[1,2-b]pyran;
b) an electron-withdrawing, non-conjugating group bonded at the 11-position of the indeno[2',3':3,4]naphtho[1,2-b]pyran; and
c) moderate to strong electron-donating groups bonded at each of the 6- and 7-positions of the indeno[2'.3':3,4] naphtho[1,2-b]pyran.

In this embodiment of the invention, each of the two moderate to strong electron-donating groups may independently comprise:

(i) the group —$OR^{8'}$, wherein $R^{8'}$ is phenyl($C_1$-$C_3$)alkyl, $C_1$-$C_6$ alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or $R^{6'}$ is the group, —CH($R^{9'}$)Q'', wherein $R^{9'}$ is hydrogen or $C_1$-$C_3$ alkyl and Q'' is —CN, —COOH, —$COOCH_3$, or —$COOCH_2CH_3$;

(ii) —N(R15)R16, wherein R15 and R16 each independently comprises hydrogen, $C_1$-$C_8$ alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, C1-C8 alkylaryl, C3-C20 cycloalkyl, C4-C20 bicycloalkyl, C5-C20 tricycloalkyl and C1-C20 alkoxyalkyl, wherein said aryl group is phenyl or naphthyl;

(iii) a nitrogen containing ring represented by the following graphic formula:

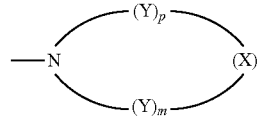

wherein Y is selected from the group consisting of —CH2-, —CH(R17)-, —C(R17)(R17)-, —CH(aryl)-, —C(aryl)2-, and —C(R17)(aryl)-, and X is selected from the group consisting of —Y—, —O—, —S—, —S(O)—, —S(O2)-, —NH—, —NR17- and —N-aryl, wherein R17 is $C_1$-$C_6$ alkyl, said aryl substituent is phenyl or naphthyl, m is the integer 1, 2 or 3, and p is the integer 0, 1, 2, or 3, provided that when p is 0, X is Y; or (iv) a group represented by one of the following graphic formulae:

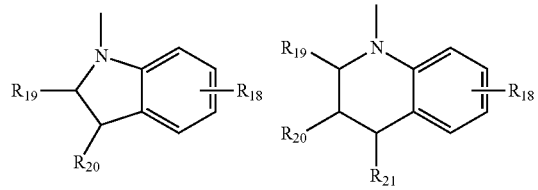

wherein R19, R20 and R21 are each hydrogen, C1-C5 alkyl, phenyl or naphthyl, or the groups R19 and R20 may come together to form a ring of 5 to 8 carbon atoms; and R18 is C1-C6 alkyl, C1-C6 alkoxy, fluoro or chloro. The two moderate to strong electron-donating groups often both comprise alkoxy, such as methoxy, groups.

The present invention further provides a photochromic material represented by the structure:

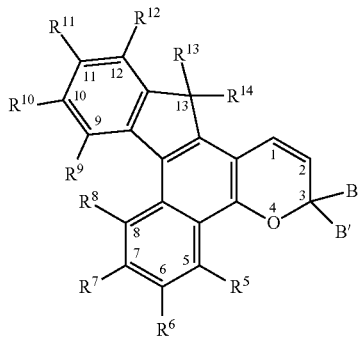

In this structure, B and B' may each independently comprise a metallocenyl group. As used herein, the term "metallocene group" refers to a group in which two cyclopentadienyl ring ligands form a "sandwich" around a metal ion, wherein each cyclopentadienyl ring is bonded to the metal ion by a pentahapto ($\eta^5$) bonding structure. Metallocene groups have the general empirical formula $(C_5H_5)_2M$, where M is a metal ion having a +2 oxidation state. As used herein, the term "metallocenyl group" refers to a metallocene group that forms or is capable of forming at least one bond with at least one other group, such as, for example, a photochromic group. Specific, non-limiting examples of metallocenyl groups that may be used in connection with the photochromic materials according to various non-limiting embodiments disclosed herein include: ferrocenyl groups, titanocenyl groups, ruthenocenyl groups, osmocenyl groups, vanadocenyl groups, chromocenyl groups, cobaltocenyl groups, nickelocenyl groups, and di-π-cyclopentadienyl-manganese groups. The metallocenyl group may be further substituted.

Alternatively, B and B' may each independently comprise:

an aryl group that is mono-substituted with a compatibilizing substituent;

9-julolidinyl, an unsubstituted, mono-, di- or tri-substituted aryl group chosen from phenyl and naphthyl, an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, wherein the aryl and heteroaromatic substituents are each independently: hydroxy, aryl, mono- or di-($C_1$-$C_{12}$) alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$) alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, e.g., methoxy, ethoxy, propoxy, isopropoxy, butoxy, pentyloxy, phenoxy, etc., mono($C_1$-$C_{12}$)alkoxy($C_1$-$C_{12}$)alkyl, halogen or —C(=O)$R^{22}$, wherein $R^{22}$ is —O$R^{23}$, —N($R^{24}$)$R^{25}$, piperidino or morpholino, wherein $R^{23}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{24}$ and $R^{25}$ are each independently $C_1$-$C_6$ alkyl, $C_5$-$C_7$ cycloalkyl or a substituted or an unsubstituted phenyl, wherein said phenyl substituents are each independently $C_1$-$C_3$ alkyl or $C_1$-$C_6$ alkoxy;

an unsubstituted or mono-substituted group chosen from pyrazolyl, imidazolyl, pyrazolinyl, imidazolinyl, pyrrolidino, phenothiazinyl, phenoxazinyl, phenazinyl and acridinyl, said wherein said substituents are each independently $C_1$-$C_{12}$ alkyl, $C_1$-$C_{12}$ alkoxy, phenyl or halogen;

a 4-substituted phenyl, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_e$— or —[O—($CH_2$)$_e$]$_f$—, wherein e is an integer ranging from 2 to 6 and f is an integer ranging from 1 to 50, and wherein the substituent is connected to an aryl group of another photochromic material;

a group represented by:

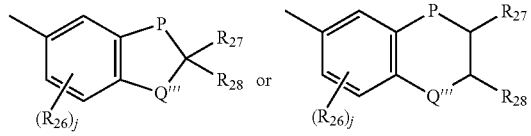

wherein P is —$CH_2$— or —O—; Q''' is —O— or substituted nitrogen, the substituted nitrogen substituents being hydrogen, $C_1$-$C_{12}$ alkyl or $C_1$-$C_{12}$ acyl, provided that when Q''' is substituted nitrogen, P is —$CH_2$—; each $R^{26}$ is independently $C_1$-$C_{12}$ alkyl, $C_1$-$C_{12}$ alkoxy, hydroxy or halogen; $R^{27}$ and $R^{28}$ are each independently hydrogen or $C_1$-$C_{12}$ alkyl; and j is an integer ranging from 0 to 2; or B and B' taken together form a fluoren-9-ylidene or mono- or di-substituted fluoren-9-ylidene, wherein said fluoren-9-ylidene substituents are each independently $C_1$-$C_{12}$ alkyl, $C_1$-$C_{12}$ alkoxy or halogen.

$R^5$, $R^8$, $R^9$ and $R^{12}$ may each independently comprise:

hydrogen, $C_1$-$C_6$ alkyl, chloro, fluoro, bromo, $C_3$-$C_7$ cycloalkyl or a unsubstituted, mono- or di-substituted phenyl, wherein said phenyl substituents are each independently $C_1$-$C_6$ alkyl or $C_1$-$C_6$ alkoxy;

—O$R^{40}$ or —OC(=O)$R^{40}$, wherein $R^{40}$ is hydrogen, amine, alkylene glycol, polyalkylene glycol, $C_1$-$C_3$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, mono($C_1$-$C_4$)alkyl substituted $C_3$-$C_7$ cycloalkyl or an unsubstituted, mono- or di-substituted phenyl, wherein said phenyl substituents are each independently $C_1$-$C_3$ alkyl or $C_1$-$C_6$ alkoxy;

a compatibilizing substituent;

a 4-substituted phenyl, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_e$— or —[O—($CH_2$)$_e$]$_f$—, wherein e is an integer ranging from 2 to 6, and f is an integer ranging from 1 to 50, and wherein the substituent is connected to an aryl group of another photochromic material;

—N($R^{41}$)$R^{42}$, wherein $R^{41}$ and $R^{42}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_8$ cycloalkyl, $C_4$-$C_{16}$ bicycloalkyl, $C_5$-$C_{20}$ tricycloalkyl or $C_1$-$C_{20}$ alkoxy($C_1$-$C_6$)alkyl, or $R^{41}$ and $R^{42}$ come together with the nitrogen atom to form a $C_3$-$C_{20}$ hetero-bicycloalkyl ring or a $C_4$-$C_{20}$ hetero-tricycloalkyl ring;

a nitrogen containing ring represented by:

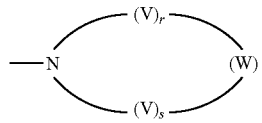

wherein each —V— is independently chosen for each occurrence from —$CH_2$—, —$CH(R^{43})$—, —$C(R^{43})_2$—, —CH(aryl)-, —$C(aryl)_2$- and —$C(R^{43})$(aryl)-, wherein each $R^{43}$ is independently $C_1$-$C_6$ alkyl and each aryl is independently phenyl or naphthyl; —W— is —V—, —O—, —S—, —S(O)—, —$SO_2$—, —NH—, —$N(R^{43})$— or —N(aryl)-; s is an integer ranging from 1 to 3; and r is an integer ranging from 0 to 3, provided that if r is 0, then —W— is the same as —V; or a group represented by:

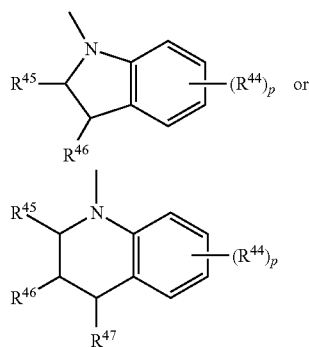

wherein each $R^{44}$ is independently $C_1$-$C_6$ alkyl, $C_1$-$C_6$ alkoxy, fluoro or chloro; $R^{45}$, $R^{46}$ and $R^{47}$ are each independently hydrogen, $C_1$-$C_6$ alkyl, phenyl or naphthyl, or $R^{45}$ and $R^{46}$ together form a ring of 5 to 8 carbon atoms, and p is an integer ranging from 0 to 3.

$R^6$ and $R^7$ may each independently comprise a moderate to strong electron-donating group as described above.

$R^{10}$ may comprise any of the groups discussed above with respect to $R^5$, $R^8$, $R^9$ and $R^{12}$ or a metallocenyl group.

$R^{11}$ typically comprises an electron-withdrawing, non-conjugating group as discussed above.

$R^{13}$ and $R^{14}$ do not form a spirocyclic group and each may independently comprise any of those groups described above as suitable for bonding at the 13-position of the indeno[2',3':3,4]naphtho[1,2-b]pyran. For example, $R^{13}$ and $R^{14}$ each independently may comprise an alkyl group or an alkoxy group; or they may comprise two methyl groups or one ethyl and one methoxy group.

As indicated above and discussed in more detail herein below, the photochromic materials according to various non-limiting embodiments disclosed herein may comprise a compatibilizing substituent. As used herein, the term "compatibilizing substituent" means an arrangement of atoms that can facilitate integration of the photochromic material into another material or solvent. For example, according to various non-limiting embodiments disclosed herein, the compatibilizing substituent may facilitate integration of the photochromic material into a hydrophilic material by increasing the miscibility of the photochromic material in water or a hydrophilic polymeric, oligomeric or monomeric material. According to other non-limiting embodiments, the compatibilizing substituent may facilitate integration of the photochromic material into a lipophilic material. Although not limiting herein, photochromic materials according to various non-limiting embodiments disclosed herein that comprise a compatibilizing substituent that facilitates integration into a hydrophilic material may be miscible in hydrophilic material at least to the extent of one gram per liter. Non-limiting examples of compatibilizing substituents include those substituents comprising a group -J, wherein -J represents the group —K (discussed below) or hydrogen.

Non-limiting examples of compatibilizing substituents that may be used in conjunction with the various non-limiting embodiments disclosed herein may be represented by:

| | | |
|---|---|---|
| -A-D-E-G-J (v); | -G-E-G-J (vi); | -D-E-G-J (vii); |
| -A-D-J (viii); | -D-G-J (ix); | -D-J (x); |
| -A-G-J (xi); | -G-J (xii); or | -A-J (xiii). |

With reference to (v)-(xiii) above, non-limiting examples of groups that -A- may represent according to various non-limiting embodiments disclosed herein include —O—, —C(=O)—, —$CH_2$—, —OC(=O)— and —NHC(=O)—, provided that if -A- represents —O—, -A- forms at least one bond with -J. Non-limiting examples of groups that -D- may represent according to various non-limiting embodiments include: (a) a diamine residue or a derivative thereof, wherein a first amino nitrogen of said diamine residue may form a bond with -A-, or a substituent or an available position on the indeno-fused naphthopyran, and a second amino nitrogen of said diamine residue may form a bond with -E-, -G- or -J; and (b) an amino alcohol residue or a derivative thereof, wherein an amino nitrogen of said amino alcohol residue may form a bond with -A-, or a substituent or an available position on the indeno-fused naphthopyran, and an alcohol oxygen of said amino alcohol residue may form a bond with -E-, -G- or -J. Alternatively, according to various non-limiting embodiments disclosed herein the amino nitrogen of said amino alcohol residue may form a bond with -E-, -G- or -J, and said alcohol oxygen of said amino alcohol residue may form a bond with -A-, or a substituent or an available position on the indeno-fused naphthopyran.

Non-limiting examples of suitable diamine residues that -D- may represent include an aliphatic diamine residue, a cyclo aliphatic diamine residue, a diazacycloalkane residue, an azacyclo aliphatic amine residue, a diazacrown ether residue, or an aromatic diamine residue. Specific non-limiting examples of diamine residues include the following:

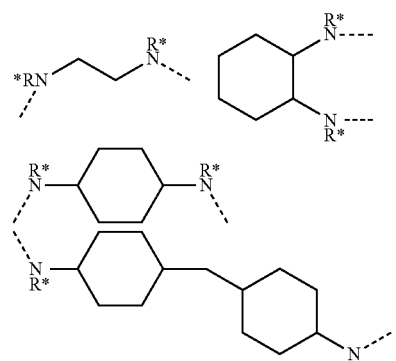

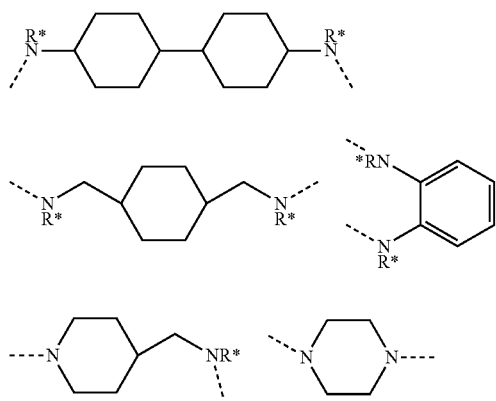

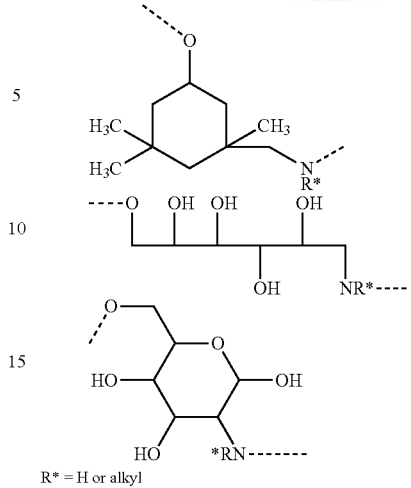

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue or an aromatic amino alcohol residue. Specific non-limiting examples of amino alcohol residues that may be used in conjunction with various non-limiting embodiments disclosed herein include the following:

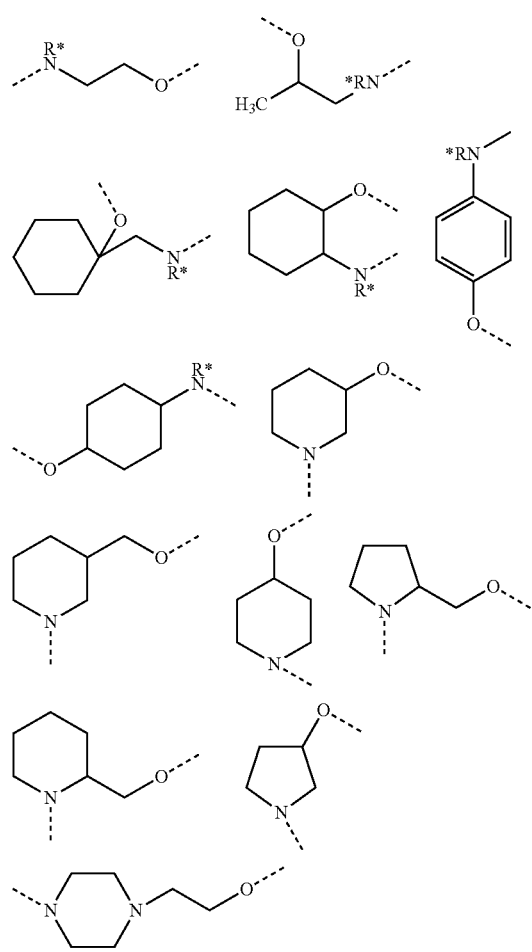

With continued reference to (v)-(xiii) above, according to various non-limiting embodiments disclosed herein, -E- may represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- may represent include an aliphatic dicarboxylic acid residue, a cycloaliphatic dicarboxylic acid residue or an aromatic dicarboxylic acid residue.

Specific non-limiting examples of dicarboxylic acid residues that may be used in conjunction with various non-limiting embodiments disclosed herein include the following:

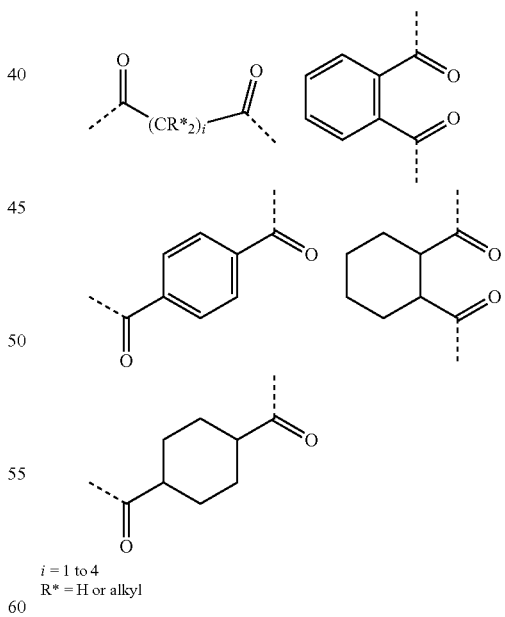

$i$ = 1 to 4
R* = H or alkyl

According to various non-limiting embodiments disclosed herein, -G- may represent: (a) a group —[(OC$_2$H$_4$)$_x$(OC$_3$H$_6$)$_y$(OC$_4$H$_8$)$_z$]—O—, wherein x, y and z are integers that are each independently chosen and range from 0 to 50, and a sum of x, y and z ranges from 1 to 50; (b) a polyol residue or a derivative thereof, wherein a first polyol oxygen of said polyol residue may form a bond with -A-, -D-, -E- or a substituent or an available position on the indeno-fused naphthopyran and a second polyol oxygen of said polyol may form a bond with -E- or -J; or (c) a combination of (a) and (b), wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- may represent include an aliphatic polyol residue, a cyclo aliphatic polyol residue or an aromatic polyol residue.

Specific non-limiting examples of polyols from which the polyol residues that -G- may represent may be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as, but not limited to, those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to, those set forth in U.S. Pat. No. 6,555,028 at col. 6, lines 13-43, which disclosure is hereby specifically incorporated by reference herein; (h) polyacrylic polyols, such as, but not limited to, those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

Referring again to (v)-(xiii) above, according to various non-limiting embodiments disclosed herein -J may represent a group —K, wherein —K represents a group, such as, but not limited to, —CH$_2$COOH, —CH(CH$_3$)COOH, —C(O)(CH$_2$), COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein w represents an integer ranging from 1 to 18. According to other non-limiting embodiments, -J may represent hydrogen that forms a bond with an oxygen or a nitrogen of a linking group to form a reactive moiety, such as, —OH or —NH. For example, according to various non-limiting embodiments disclosed herein, -J may represent hydrogen, provided that if -J represents hydrogen, -J is bonded to an oxygen of -D- or -G-, or a nitrogen of -D-.

As previously discussed, -G- may represent a residue of a polyol, which is defined herein to include hydroxy-containing carbohydrates, such as, those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -A-, such as, a carboxylic acid or a methylene halide, a precursor of polyalkoxylated group, such as, polyalkylene glycol, or a hydroxyl substituent of the indeno-fused naphthopyran. The polyol may be represented by R'—(OH)$_g$ and the residue of the polyol may be represented by the formula —O—R'—(OH)$_{g-1}$, wherein R' is the backbone or main chain of the polyhydroxy compound and g is at least 2.

Further, as discussed above, one or more of the polyol oxygens of -G- may form a bond with -J (i.e., forming the group -G-J). For example, although not limiting herein, wherein the compatibilizing substituent comprises the group -G-J, if -G- represents a polyol residue and -J represents a group —K that contains a carboxyl terminating group, -G-J may be produced by reacting one or more polyol hydroxyl groups to form the group —K (for example, as discussed with respect to Reactions B and C at col. 13, line 22 to col. 16, line 15 of U.S. Pat. No. 6,555,028, which disclosure is hereby specifically incorporated by reference herein) to produce a carboxylated polyol residue.

Alternatively, if -J represents a group —K that contains a sulfo or sulfono terminating group, although not limiting herein, -G-J may be produced by the acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively.

The photochromic materials of the present invention transition quickly from their optically colorless state to their colored state and/or from their colored state to their optically colorless state, that is, a photochromic material having "fast" activation and/or fade rates. Throughout the present disclosure, the term "fade rate" represents a kinetic rate value that may be expressed by the T$_{1/2}$ value of the photochromic material. "Fade rate" is a measurement of the rate at which the photochromic material transforms from the colored, activated-state form to the optically clear, ground-state form. The fade rate of a photochromic material may be measured, for example, by activating a photochromic material to saturation under controlled conditions in a given matrix, measuring its activated steady state absorbance (i.e., its saturated optical density) and then determining the length of time it takes for the absorbance of the photochromic material to decrease to one-half the activated steady state absorbance value. As measured in this fashion, the fade rate may be designated by T$_{1/2}$, with units of seconds. Thus, when the fade rate is said to be fast or faster, the photochromic material changes from the colored state to the optically colorless state at a faster rate. The faster fade rate may be indicated, for example, by a lower T$_{1/2}$ value for the photochromic material. That is, as the fade rate becomes faster, the length of time for the absorbance to decrease to one-half the initial activated absorbance value will become shorter.

It will be appreciated by those skilled in the art that the fade rate of the photochromic material may be dependent somewhat on the media into which the photochromic material is incorporated. As used herein in relation to a photochromic material in a media, the term "incorporated" means physically and/or chemically combined with. In the present disclosure, all photochromic performance data, including fade rate values as denoted by T$_{1/2}$ values and bathochromic shift values, disclosed herein are measured using a standard protocol involving incorporation of the photochromic material into a polymer test chip comprising a methacrylate polymer, unless specifically noted otherwise. One skilled in the art will recognize that although exact values for fade rates and other photochromic performance data, such as, for example, bathochromic shift data, may vary depending upon the medium into which the photochromic material is incorporated, the photochromic performance data presented herein may be illustrative of relative rates and shifts that may be expected for the photochromic material when incorporated into other media.

The photochromic materials of the present invention comprising the indeno[2',3':3,4]naphtho[1,2-b]pyran and an electron-withdrawing, non-conjugating group bonded at the 11-position of the indeno-fused naphthopyran typically demonstrate a faster fade rate as compared to a comparable indeno-fused naphthopyran without an electron-withdrawing, non-conjugating group bonded at the 11-position thereof.

The photochromic materials of the present may be chosen from:
  a) 3,3-di(4-methoxyphenyl) -6,7-dimethoxy-11-trifluoromethyl-13,13-dimethyl-3H,13H-indeno[2',3':3,4]naphtho[1,2-b]pyran;
  b) 3,3-di(4-methoxyphenyl) -6-methoxy-7-morpholino-11-trifluoromethyl-13,13-dimethyl-3H,13H-indeno[2',3':3,4]naphtho[1,2-b]pyran;
  c) 3-(4-methoxyphenyl)-3-(4-(2-hydroxyethoxy)phenyl)-6,7-dimethoxy-11-trifluoromethyl-13,13-dimethyl-3H,13H-indeno[2',3':3,4]naphtho[1,2-b]pyran;
  d) 3-(4-methoxyphenyl)-3-(4-(2-hydroxyethoxy)phenyl)-6-methoxy-7-morpholino-11-trifluoromethyl-13,13-dimethyl-3H,13H-indeno[2',3':3,4]naphtho[1,2-b]pyran;
  e) 3-(4-methoxyphenyl)-3-(4-fluorophenyl)-6,7-dimethoxy- 11-trifluoromethyl-13,13-dimethyl-3H,13H-indeno[2',3':3,4]naphtho[1,2-b]pyran;
  f) 3-(4-morpholinophenyl)-3-(4-fluorophenyl)-6,7-dimethoxy-11-trifluoromethyl-13,13-dimethyl-3H,13H-indeno[2',3':3,4]naphtho[1,2-b]pyran;
  g) 3-(4-methoxyphenyl)-3-(4-morpholinophenyl)-6,7-dimethoxy-11-trifluoromethyl-13,13-dimethyl-3H,13H-indeno[2',3':3,4]naphtho[1,2-b]pyran;
  h) 3-(4-methoxyphenyl)-3-(4-butoxyphenyl)-6,7-dimethoxy-11-trifluoromethyl-13,13-dimethyl-3H,13H-indeno[2',3':3,4]naphtho[1,2-b]pyran;
  i) 3,3-di-(4-(2-methoxyethoxy)phenyl)-6,7-dimethoxy-11-trifluoromethyl-13,13-dimethyl-3H,13H-indeno[2',3':3,4]naphtho[1,2-b]pyran;
  j) 3-(4-methoxyphenyl)-3-(4-ethoxyphenyl)-6,7-dimethoxy-11-trifluoromethyl-13,13-dimethyl-3H,13H-indeno[2',3':3,4]naphtho[1,2-b]pyran;
  k) 3-(4-methoxyphenyl)-3-(4-butoxyphenyl)-6-methoxy-7-morpholino-11-trifluoromethyl-13,13-dimethyl-3H,13H-indeno[2',3':3,4]naphtho[1,2-b]pyran;
  l) 3,3-di-(4-fluorophenyl)-6-methoxy-7-morpholino-11-trifluoromethyl-13-butyl-13-(2-(2-hydroxyethoxy)ethoxy)-3H,13H-indeno[2',3':3,4]naphtho[1,2-b]pyran; and
  m) mixtures thereof.

The photochromic materials of the present invention typically have a closed-form absorption spectrum for electromagnetic radiation that is bathochromically shifted, as compared to a closed-form absorption spectrum for electromagnetic radiation of photochromic materials comprising a comparable indeno[2',3':3,4]naphtho[1,2-b]pyran without the electron-withdrawing, non-conjugating group at the 11-position thereof. By "bathochromically shifted" is meant that photochromic materials can have a closed-form absorption spectrum for electromagnetic radiation that is shifted to longer wavelengths. As used herein the term "closed-form absorption spectrum" refers to the absorption spectrum of the photochromic material in the closed-form or unactivated state. In certain applications, the closed-form absorption spectrum of the photochromic material can be shifted such that the photochromic material may absorb sufficient electromagnetic radiation having a wavelength greater than 390 nm to permit the photochromic material to transform from the closed-form to an open-form. Such a bathochromic shift allows for a lower directional dependency.

The photochromic materials according to the present invention may further comprise an organic material into which the indeno[2',3':3,4]naphtho[1,2-b]pyran is incorporated. Suitable organic materials include, for example, a polymeric, oligomeric or monomeric material. These photochromic materials may then be used, for example and without limitation, to form photochromic articles, such as, optical elements, and coating compositions that may be applied to various substrates. As used herein, the terms "polymer" and "polymeric material" refer to homopolymers and copolymers (e.g., random copolymers, block copolymers, and alternating copolymers), as well as blends and other combinations thereof. As used herein, the terms "oligomer" and "oligomeric material" refer to a combination of two or more monomer units that are capable of reacting with additional monomer unit(s). As used herein, the term "incorporated into" means physically and/or chemically combined with. For example, the photochromic materials according to various non-limiting embodiments disclosed herein may be physically combined with at least a portion of an organic material, for example and without limitation, by mixing or imbibing the photochromic material into the organic material; and/or chemically combined with at least a portion of an organic material, for example and without limitation, by copolymerization or otherwise bonding the photochromic material to the organic material. Further, it is contemplated that the photochromic materials according to the present invention may each be used alone in the photochromic articles disclosed herein, or may be used in combination with other photochromic materials. For example, the photochromic materials of the present invention may be used in conjunction with conventional photochromic materials having activated-state form absorption maxima within the range of 300 to 1000 nanometers, for example, from 400 to 800 nanometers.

Further, the photochromic materials according of the present invention may be used in conjunction with a complementary conventional polymerizable or a compatibilized photochromic compound, such as, for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

As discussed above, the photochromic materials may contain a mixture of photochromic compounds. For example, mixtures of photochromic materials may be used to attain certain activated colors, such as, a near neutral gray or near neutral brown. U.S. Pat. No. 5,645,767, col. 12, line 66 to col. 13, line 19, describes the parameters that define neutral gray and brown colors and which disclosure is specifically incorporated by reference herein.

The photochromic material may be incorporated into a portion of the organic material by blending and/or bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof.

When the photochromic material further comprises a polymeric material, examples of polymeric materials that may be used therein include, without limitation: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as, ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as, poly(methyl methacrylate); poly(oxyalkylene)-dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(α-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate and butyl acrylate. Also contemplated are copolymers of the aforementioned monomers, combinations, and blends of the aforementioned polymers and copolymers with other polymers, e.g., to form interpenetrating network products.

When transparency of the photochromic composition is desired, the organic material may be a transparent polymeric material. For example, the polymeric material may be an optically clear polymeric material prepared from a thermoplastic polycarbonate resin, such as, the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly (vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to certain non-limiting embodiment, the polymeric materials may be an optical resins sold by PPG Industries, Inc. under the CR-designation, e.g., CR-307, CR-407, and CR-607.

Often the organic material may be a polymeric material chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

Further, it will be appreciated by those skilled in the art that the photochromic materials disclosed herein may further comprise other additives that aid in the processing and/or performance of the composition or a coating or article derived therefrom. Non-limiting examples of such additives include polymerization inhibitors, solvents, light stabilizers (such as, but not limited to, ultraviolet light absorbers and light stabilizers, such as, hindered amine light stabilizers (HALS)), heat stabilizers, mold release agents, rheology control agents, leveling agents (such as, but not limited to, surfactants), free radical scavengers, adhesion promoters (such as, hexanediol diacrylate and coupling agents), and combinations and mixtures thereof.

As previously discussed, the present invention further contemplates photochromic articles, such as optical elements, comprising a substrate and any of the photochromic materials disclosed herein, in contact with at least a portion of the substrate. As used herein, the term "in contact with" means associated with, either directly or indirectly through another material or structure. Further, as used herein in the context of a coating being "on" a surface or object, the term "on" means that the subject coating is connected to the surface or object such that the subject coating is supported or carried by the surface or object. For example, a coating that is "on" a surface may be applied directly over the surface or it may be applied over one or more other coatings, at least one of which is applied directly over the surface.

As used herein, the term "optical" means pertaining to or associated with light and/or vision. The optical elements according to various non-limiting embodiments disclosed herein may include, without limitation, ophthalmic elements, display elements, windows, mirrors, and liquid crystal cell elements. As used herein, the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect or enhance (cosmetically or otherwise) vision, including without limitation, contact lenses and other intraocular elements, magnifying lenses, protective lenses, visors, goggles, as well as, lenses for optical instruments (for example, cameras and telescopes). As used herein, the term "display" means the visible or machine-readable representation of information in words, numbers, symbols, designs or drawings. Non-limiting examples of display elements include screens, monitors, and security elements, such as, security marks. As used herein, the term "window" means an aperture adapted to permit the transmission of radiation therethrough. Non-limiting examples of windows include automotive and aircraft transparencies, windshields, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display.

According to various non-limiting embodiments disclosed herein wherein the substrate of the photochromic article comprises a polymeric material, the photochromic material may be in contact with at least a portion of the substrate by incorporating the photochromic material into at least a portion of the polymeric material of the substrate, or by incorporating the photochromic material into at least a portion of the oligomeric or monomeric material from which the substrate is formed. For example, the photochromic article may be formed from a photochromic material, such as those discussed above, by the cast-in-place method wherein the photochromic material is incorporated into at least a portion of the polymeric material of the substrate by blending and/or bonding the photochromic material with at least a portion of the polymeric material prior to forming the substrate, or by incorporating the photochromic material into at least a portion of the oligomeric or monomeric material from which the polymeric material of the substrate is formed prior to forming the substrate. The photochromic material may alternatively be incorporated into the polymeric material of the substrate by imbibition. Imbibition and the cast-in-place method are discussed below in more detail.

The photochromic material may also be in contact with at least a portion of the substrate of the photochromic article as part of a coating that is applied to at least a portion of a substrate. As used herein, the term "coating" means a structure comprising one or more complete or partial layers (which may or may not have a uniform composition and/or cross-sectional thickness) derived from flowable compositions. The flowable compositions from which coatings may be formed include, for example, liquid or powder compositions, which may be applied to the substrate using methods such as those discussed herein below. In these methods of preparation, the substrate may be a polymeric substrate or an inorganic substrate (such as, but not limited to, a glass substrate). Examples of monomers and polymers that may be used to form the polymeric substrates include, but are not limited to, those monomers and polymers discussed above that may be useful in forming the photochromic compositions disclosed herein.

The substrate may be an ophthalmic substrate. As used herein, the term "ophthalmic substrate" refers to lenses, partially formed lenses, and lens blanks. Non-limiting examples of organic materials from which ophthalmic substrates may be formed include, but are not limited to, art-recognized polymers that are useful in forming transparent or optically clear castings for optical applications (such as those previously discussed).

Other non-limiting examples of organic materials suitable for use in forming the substrates include both synthetic and natural organic materials, including without limitation: opaque or translucent polymeric materials, natural and synthetic textiles, and cellulosic materials. Non-limiting examples of inorganic materials suitable for use in forming substrates include inorganic oxide-based glasses, minerals, ceramics, and metals. For example, the substrate may be a ceramic, metal or mineral substrate that has been polished to form a reflective surface. In other non-limiting embodiments, a reflective coating or layer may be deposited or otherwise applied to a surface of an inorganic or an organic substrate to make it reflective or enhance its reflectivity.

The substrate may comprise a protective coating on at least a portion of its surface. As used herein, the term "protective coating" refers to coatings or films that can prevent wear or abrasion, provide a transition in properties from one coating or film to another, protect against the effects of polymerization reaction chemicals and/or protect against deterioration due to environmental conditions, such as, moisture, heat, ultraviolet light, oxygen, etc. For example, commercially available thermoplastic polycarbonate ophthalmic lens substrates are often sold with an abrasion-resistant coating already applied to their surfaces because these surfaces tend to be readily scratched, abraded or scuffed. An example of one such polycarbonate lens substrate is sold under the trademark GENTEX (by Gentex Optics). Non-limiting examples of abrasion-resistant coatings include, abrasion-resistant coatings comprising silanes, abrasion-resistant coatings comprising radiation-cured acrylate-based thin films, abrasion-resistant coatings based on inorganic materials, such as, silica, titania and/or zirconia, and combinations thereof. For example, the protective coating may comprise a first coating of a radiation-cured acrylate-based thin film and a second coating comprising a silane. Non-limiting examples of commercial protective coatings products include SILVUE® 124 and HI-GARD® coatings, commercially available from SDC Coatings, Inc. and PPG Industries, Inc., respectively.

The photochromic material according to various non-limiting embodiments of the present invention discussed above may be incorporated into at least a portion of a coating composition prior to application of the coating composition to the substrate, or alternatively, a coating composition may be applied to the substrate, at least partially set, and thereafter the photochromic material may be imbibed into at least a portion of the coating. As used herein with reference to coatings, coating compositions, or components thereof, the terms "set" and "setting" are intended to include processes, such as, but not limited to, curing, polymerizing, cross-linking, cooling, and drying.

Specific non-limiting examples of coating compositions into which the photochromic materials may be incorporated include, but are not limited to, those coating compositions known in the art for use in connection with photochromic materials. Non-limiting examples of coating compositions into which the photochromic materials may be incorporated include the mono-isocyanate containing coating compositions disclosed in U.S. Pat. No. 6,916,537 ("the '537 Patent") at col. 3, lines 1 to 12, which comprises (in addition to a photochromic material) a reaction product (non-limiting examples which are set forth in the '537 Patent at col. 7, lines 4-37) of a polyol comprising at least one carbonate group (non-limiting examples of which are set forth in the '537 Patent at col. 7, line 38 to col. 8, line 49) and an isocyanate comprising at least one reactive isocyanate group and at least one polymerizable double bond (non-limiting examples of which are set forth in the '537 Patent at col. 8, line 50 to col. 9, line 44), and which optionally comprises an addition copolymerizable monomer (non-limiting examples of which are set forth in the '537 Patent at col. 11, line 47 to col. 20, line 43). The above-referenced disclosure of the '537 Patent is hereby specifically incorporated by reference herein.

Other non-limiting examples of coating compositions into which the photochromic materials may be incorporated include the poly(urea-urethane) compositions disclosed in U.S. Pat. No. 6,531,076, at col. 3, line 4 to col. 10, line 49, which disclosure is hereby specifically incorporated by reference herein. Still other non-limiting examples of coating compositions into which the photochromic materials may be incorporated include the polyurethane compositions disclosed in U.S. Pat. No. 6,187,444, at col. 2, line 52 to col. 12, line 15, which disclosure is hereby specifically incorporated by reference herein.

Yet other non-limiting examples of coating compositions into which the photochromic materials may be incorporated include the poly(meth)acrylic coating compositions described in U.S. Pat. No. 6,602,603, at col. 2, line 60 to col. 7, line 50; the aminoplast resin coating compositions described in U.S. Pat. No. 6,506,488, at col. 2, line 43 to col. 12, line 23 and U.S. Pat. No. 6,432,544, at col. 2, line 32 to col. 14, line 5; the polyanhydride coating compositions described in U.S. Pat. No. 6,436,525, at col. 2, line 15 to col. 11, line 60; the epoxy resin coating compositions described in U.S. Pat. No. 6,268,055, at col. 2, line 63 to col. 17, line 3; and the alkoxyacrylamide coating compositions descried in U.S. Pat. No. 6,060,001, at col. 2, line 6 to col. 5, line 39. The above-referenced disclosures are hereby specifically incorporated by reference herein.

Further, it will be appreciated by those skilled in the art that the photochromic coating compositions may further comprise other additives that aid in the processing and/or performance of the composition or coating derived therefrom. Non-limiting examples of such additives include photoinitiators, thermal initiators, polymerization inhibitors, solvents, light stabilizers (such as, but not limited to, ultraviolet light absorbers and light stabilizers, such as, hindered amine light stabilizers (HALS)), heat stabilizers, mold release agents, rheology control agents, leveling agents (such as, but not limited to, surfactants), free radical scavengers, adhesion promoters (such as, hexanediol diacrylate and coupling agents), and combinations and mixtures thereof.

An at least partial coating comprising the photochromic material may be in contact with at least a portion of a substrate of a photochromic article, for example, by applying a coating composition comprising the photochromic material to at least a portion of a surface of the substrate and at least partially setting the coating composition. Additionally or alternatively, the at least partial coating comprising the photochromic material may be connected to the substrate, for example, through one or more additional at least partial coatings. For example, while not limiting herein, an additional coating composition may be applied to a portion of the surface of the substrate, at least partially set, and thereafter a coating composition comprising the photochromic material may be applied over the additional coating and at least partially set. Non-limiting methods of applying coatings compositions to substrates are discussed herein below.

Non-limiting examples of additional coatings and films that may be used in conjunction with the photochromic articles disclosed herein include primer or compatibilizing coatings; protective coatings, including transitional coatings, abrasion-resistant coatings and other coatings that protect against the effects of polymerization reaction chemicals and/or protect against deterioration due to environmental conditions, such as, moisture, heat, ultraviolet light, and/or oxygen (e.g., UV-shielding coatings and oxygen barrier coatings); anti-reflective coatings; conventional photochromic coating; polarizing coatings and polarizing stretched-films; and combinations thereof.

Non-limiting examples of primer or compatibilizing coatings that may be used in conjunction with various non-limiting embodiments disclosed herein include coatings comprising coupling agents, at least partial hydrolysates of coupling agents, and mixtures thereof. As used herein, the term "coupling agent" means a material having a group capable of reacting, binding and/or associating with a group on a surface. Coupling agents according to various non-limiting embodiments disclosed herein may include organometallics, such as, silanes, titanates, zirconates, aluminates, zirconium aluminates, hydrolysates thereof, and mixtures thereof. As used herein, the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating may aid in creating a gradient in hardness between a relatively hard coating (such as, an abrasion-resistant coating) and a relatively soft coating (such as, a photochromic coating). Non-limiting examples of transitional coatings include radiation-cured, acrylate-based thin films as described in U.S. Patent Application Publication No. 2003/0165686 at paragraphs [0079]-[0173], which disclosure is hereby specifically incorporated by reference herein.

As used herein, the term "abrasion-resistant coating" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion-resistant coatings include abrasion-resistant coatings comprising organosilanes, organosiloxanes, abrasion-resistant coatings based on inorganic materials, such as, silica, titania and/or zirconia, and organic abrasion-resistant coatings that are ultraviolet light curable.

Non-limiting examples of antireflective coatings include a monolayer coating or multilayer coatings of metal oxides, metal fluorides, or other such materials, which may be deposited onto the articles disclosed herein (or onto self supporting films that are applied to the articles), for example, through vacuum deposition, sputtering, etc.

Non-limiting examples of polarizing coatings and polarizing stretched-films include, but are not limited to, polarizing coatings (such as those described in U.S. Patent Application Publication No. 2005/0151926, at paragraphs [0029]-[0116], which disclosure is hereby specifically incorporated by reference herein), and polarizing stretched-films comprising dichroic compounds that are known in the art.

As discussed above, an additional at least partial coating or film may be formed on the substrate prior to forming the coating comprising the photochromic material on the substrate. For example, a primer or compatibilizing coating may be formed on the substrate prior to applying the coating composition comprising the photochromic material. Additionally or alternatively, one or more additional at least partial coating(s) may be formed on the substrate after forming the coating comprising the photochromic material on the substrate, for example, as an overcoating on the photochromic coating.

For example, a transitional coating may be formed over the coating comprising the photochromic material, and an abrasion-resistant coating may then be formed over the transitional coating.

For example, there is provided a photochromic article comprising a substrate (such as, but not limited to a piano-concave or a piano-convex ophthalmic lens substrate), which comprises an abrasion-resistant coating on at least a portion of a surface thereof; a primer or compatibilizing coating on at least a portion of the abrasion-resistant coating; a photochromic coating comprising a photochromic material, according to various non-limiting embodiments disclosed herein, on at least a portion of the primer or compatibilizing coating; a transitional coating on at least a portion of the photochromic coating; and an abrasion-resistant coating on at least a portion of the transitional coating. Further, according to other non-limiting embodiments, the photochromic article may also comprise, for example, an antireflective coating that is connected to a surface of the substrate and/or a polarizing coating or film that is connected to a surface of the substrate.

When the substrate comprises a polymeric material, the photochromic material may be connected to at least a portion of a substrate by in-mold casting. According to this embodiment, a coating composition comprising the photochromic material, which may be a liquid coating composition or a powder coating composition, may be applied to the surface of a mold and at least partially set. Thereafter, a polymer solution or melt, or oligomeric or monomeric solution or mixture may be cast over the coating and at least partially set. After setting, the coated substrate may be removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

When the substrate comprises a polymeric material or an inorganic material, such as, for example, glass, the photochromic material may be connected to at least a portion of a substrate by a coating process. Non-limiting examples of suitable coating processes include spin-coating, spray coating (e.g., using a liquid or a powder coating compositions), curtain coating, roll coating, spin and spray coating, dip coating, over-molding, and combinations thereof. For example, the photochromic material may be connected to the substrate by over-molding. In this instance, a coating composition comprising the photochromic material (examples of which coatings are discussed above) may be applied to a mold and then a substrate may be placed into the mold such that the substrate contacts the coating causing it to spread over at least a portion of the surface of the substrate. Thereafter, the coating composition may be at least partially set and the coated substrate may be removed from the mold. Alternatively, the over-molding process may comprise placing the substrate into a mold such that an open region is defined between the substrate and the mold, and thereafter injecting a coating composition comprising the photochromic material into the open region. Thereafter, the coating composition may be at least partially set and the coated substrate may be removed from the mold. The photochromic material may also be connected to a substrate by spin-coating a coating composition comprising the photochromic material onto the substrate, for example, by rotating the substrate and applying the coating composition to the substrate while it is rotating and/or by applying the coating composition to the substrate and subsequently rotating the substrate.

Additionally or alternatively, a coating composition (with or without a photochromic material) may be applied to a substrate (for example, by any of the foregoing coating processes), the coating composition may be at least partially set, and thereafter, a photochromic material may be imbibed (as previously discussed) into the coating.

As discussed above, after forming the photochromic coating, at least a portion of the photochromic coating may be at least partially set. For example, at least partially setting at least a portion of the photochromic coating may comprise exposing the photochromic coating to at least one of electromagnetic radiation and thermal radiation to at least partially dry, polymerize and/or cross-link one or more components of the coating composition.

When the substrate comprises a polymeric material or an inorganic material, such as, for example, glass, the photochromic material may be applied to at least a portion of a substrate by lamination. A self-supporting film or sheet comprising the photochromic material may be adhered or otherwise connected to a portion of the substrate, with or without an adhesive and/or the application of heat and pressure. Optionally, thereafter a protective coating may be applied over the film; or a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include, for example and without limitation, combining a photochromic material with a polymeric or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, prior to connecting the photochromic material to at least a portion of the substrate by coating or lamination, a primer or compatibilizing coating (such as those discussed above) may be formed on at least a portion of the surface of the substrate to enhance one or more of the wetting, adhesion, and/or chemical compatibility of the photochromic coating with the substrate. Non-limiting examples of suitable primer or compatibilizing coatings and methods of making the same are disclosed above. Still further, as previously discussed according to various non-limiting embodiments disclosed herein, the substrate may comprise an abrasion-resistant coating on at least a portion of its surface.

Prior to applying any coating or film to the substrate, for example, prior to applying the photochromic material to at least a portion of the surface of the substrate by coating and/or lamination or prior to applying a primer or compatibilizing coating to the substrate, the surface may be cleaned and/or treated to provide a clean surface and/or a surface that may enhance adhesion of the photochromic coating to the substrate. Effective cleaning and treatments may include, but are not limited to, ultrasonic washing with an aqueous soap/detergent solution; cleaning with an aqueous mixture of organic solvent, e.g., a 50:50 mixture of isopropanol:water or ethanol:water; UV treatment; activated gas treatment, e.g., treatment with low temperature plasma or corona discharge; and chemical treatment that results in hydroxylation of the substrate surface, e.g., etching of the surface with an aqueous solution of alkali metal hydroxide, e.g., sodium or potassium hydroxide, which solution can also contain a fluorosurfactant. Generally, the alkali metal hydroxide solution is a dilute aqueous solution, e.g., from 5 to 40 weight percent, more typically from 10 to 15 weight percent, such as, 12 weight percent, alkali metal hydroxide. See, for example, U.S. Pat. No. 3,971,872, column 3, lines 13 to 25; U.S. Pat. No. 4,904,525, column 6, lines 10 to 48; and U.S. Pat. No. 5,104,692, column 13, lines 10 to 59, which describe surface treatments of polymeric organic materials. The foregoing disclosures are specifically incorporated herein by reference.

Surface treatment of the substrate may be a low temperature plasma treatment. Although not limiting herein, this method allows treatment of the surface to enhance adhesion of a coating formed thereon, and may be a clean and efficient way to alter the physical surface, e.g., by roughening and/or chemically altering the surface without affecting the rest of the article. Inert gases, such as, argon, and reactive gases, such as, oxygen, may be used as the plasma gas. Inert gases may roughen the surface, while reactive gases, such as, oxygen may both roughen and chemically alter the surface exposed to the plasma, e.g., by producing hydroxyl or carboxyl units on the surface. According to one non-limiting embodiment, oxygen may be used as the plasma gas. Although not limiting herein, it is considered that oxygen may provides a slight, but effective, physical roughening of the surface along with a slight, but effective, chemical modification of the surface. As will be appreciated by those skilled in the art, the extent of the surface roughening and/or chemical modification will be a function of the plasma gas and the operating conditions of the plasma unit (including the length of time of the treatment).

The surface of the substrate subjected to plasma treatment may be at room temperature or may be preheated slightly prior to or during plasma treatment. The temperature of the surface to be subjected to a plasma treatment may be maintained at a temperature below a temperature at which the surface may be adversely affected by the plasma (other than the intended increase in surface area by roughening and slight chemical modification). One skilled in the art can readily select the operating conditions of the plasma unit, vis-à-vis, the plastic substrate treated, to achieve an improvement in the adhesion of a superimposed film/coating on the plasma treated surface.

Various non-limiting embodiments disclosed herein further contemplate the use of various combinations of the foregoing methods to form photochromic articles. For example, a photochromic material may be in contact with a substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating, and/or lamination methods discussed above.

The photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be substantially clear or colorless when the photochromic material is in the ground-state form and may exhibit a desired resultant color when the photochromic material is in the activated-state form. The precise amount of the photochromic material to be utilized in the various photochromic compositions, photochromic coatings and coating compositions, and photochromic articles described herein is not critical provided that a sufficient amount is used to produce the desired effect. It should be appreciated that the particular amount of the photochromic material used may depend on a variety of factors, such as, but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that may be incorporated into an organic material may range from 0.01 to 40 weight percent based on the weight of the organic material.

The present invention will be better understood when read in conjunction with the following non-limiting examples. The procedures set forth in the Examples below are not intended to be limiting herein, as those skilled in the art will appreciate that modifications to the procedures set forth in the Examples, as well as other procedures not described in the Examples, may be useful in preparing photochromic materials according to the present invention.

EXAMPLES

In Part 1 of the Examples, the synthesis procedures used to make photochromic materials according to various non-limiting embodiments disclosed herein are set forth in Examples 1-2 and the procedures used to make comparative photochromic materials are described in Comparative Examples 1-2. In Part 2, the preparation of the test chips and test procedures are described. In Part 3, the test results are described.

Part 1: Photochromic Materials—Synthesis

Example 1

Step 1

4-Trifluoromethylbenzoyl chloride (200 grams), 1,2-dimethoxybenzene (128 mL), and dichloromethane (1800 mL) were combined in a reaction flask under a nitrogen atmosphere. Tin (IV) chloride (168 mL) was added to the reaction mixture slowly drop-wise over 45 minutes. The reaction mixture was heated to reflux for 11 hours. It was subsequently cooled to room temperature and slowly poured into a mixture of 200 mL of hydrochloric acid and 1800 mL of ice water. The layers were phase separated. The organic layer was washed with 4 portions of water (1 L each) and then with 1.5 L of 20% saturated aqueous sodium hydroxide (w/v). The organic layer was dried over anhydrous sodium sulfate and then concentrated by rotary evaporation. The residue was recrystallized in 1 L of 15% ethyl acetate/85% hexanes. The crystalline solid was collected by vacuum filtration yielding 132 grams of 3,4-dimethoxy-4'-trifluoromethylbenzophenone. This material was not purified further but was used directly in the next step.

Step 2

3,4-dimethoxy-4'-trifluoromethylbenzophenone from Step 1 (129 grams), potassium tert-butoxide (93.5 grams), and toluene (1290 mL) were combined in a reaction flask under a nitrogen atmosphere. Dimethyl succinate (95 mL) was added to the reaction mixture drop-wise over 45 minutes. The reaction mixture was then heated to 60° C. for 3 hours. Upon cooling to room temperature, the reaction mixture was poured into ice water (1500 mL). The layers were phase separated and the aqueous layer was washed with 2 portions of ethyl ether (1 L each). The organic layers were discarded and the aqueous layer was acidified with concentrated hydrochloric acid to pH 1. Ethyl acetate (1 L) was added while stirring and then the layers were phase separated. The aqueous layer was extracted with 2 portions of ethyl acetate (1 L each). The organic layers were combined and dried over magnesium sulfate and then subsequently concentrated by rotary evaporation. The resulting orange solid was slurried in 1 L of 15% ethyl acetate/85% hexanes. The solid was collected by vacuum filtration yielding 166 grams of a mixture of (E and Z) 3-methoxycarbonyl-4-(4-trifluoromethyl)phenyl-4-(3,4-dimethoxyphenyl)-3-butenoic acid. This material was not purified further but was used directly in the next step.

Step 3

The product from Step 2 (a mixture of (E and Z) 3-methoxycarbonyl-4-(4-trifluoromethyl)phenyl-4-(3,4-dimethoxyphenyl)-3-butenoic acid, 84 grams) and acetic anhydride (252 mL) were combined in a reaction flask and heated to reflux for 5 hours.

Upon cooling to room temperature, the reaction mixture was concentrated by rotary evaporation. The residue was dissolved in ethyl acetate (500 mL) and subsequently poured into a mixture of saturated aqueous sodium bicarbonate and ice (2 L). The layers were phase separated. The organic layer was dried over magnesium sulfate and concentrated by rotary evaporation. The resulting residue was recrystallized in 500 mL of 60% methyl tert-butyl ether/40% hexanes. The crystalline solid was collected by vacuum filtration yielding 35 grams of 1-(4-trifluoromethylphenyl)-2-methoxycarbonyl-4-acetoxy-6,7-dimethoxynaphthalene and 1-(3,4-dimethoxyphenyl)-2-methoxycarbonyl-4-acetoxy-6-trifluoromethylnaphthalene. This material was not purified further but was used directly in the next step.

Step 4

The mixture from Step 3 (1-(4-trifluoromethylphenyl)-2-methoxycarbonyl-4-acetoxy-6,7-dimethoxynaphthalene and 1-(3,4-dimethoxyphenyl)-2-methoxycarbonyl-4-acetoxy-6-trifluoromethylnaphthalene, 64 grams) was weighed into a reaction flask under a nitrogen atmosphere and 1280 mL of anhydrous tetrahydrofuran was added. A 3.0M solution of methyl magnesium chloride in tetrahydrofuran (286 mL) was added to the reaction mixture over 1 hour. The reaction mixture was heated to reflux for 3.5 hours. Upon cooling to room temperature, the reaction mixture was slowly poured into saturated aqueous ammonium chloride and ice (1.5 L) while stirring. The layers were phase separated and then the aqueous layer was extracted with 2 portions of ethyl acetate (1 L each). The organic layers were combined and washed with saturated aqueous sodium bicarbonate (1.5 L) The organic layer was dried over magnesium sulfate and concentrated by rotary evaporation to a pink solid. The solid was slurried in 15% ethyl acetate/85% hexanes and collected by vacuum filtration yielding 52 grams of 1-(4-trifluoromethylphenyl)-2-(dimethylhydroxymethyl)-4-hydroxy-6,7-dimethoxynaphthalene and 1-(3,4-dimethoxyphenyl)-2-(dimethylhydroxymethyl)-4-hydroxy-6-trifluoromethylnaphthalene. This material was not purified further but was used directly in the next step.

Step 5

The products from Step 4 (1-(4-trifluoromethylphenyl)-2-(dimethylhydroxymethyl)-4-hydroxy-6,7-dimethoxynaphthalene and 1-(3,4-dimethoxyphenyl)-2-(dimethylhydroxymethyl)-4-hydroxy-6-trifluoromethylnaphthalene, 51.7 grams) were placed in a reaction flask equipped with a Dean-Stark trap and 775 mL of toluene was added. The reaction mixture was stirred under a nitrogen atmosphere and dodecylbenzene sulfonic acid (8.3 grams) was added. The reaction mixture was heated to reflux for 5 hours. Upon cooling to room temperature the reaction mixture was concentrated by rotary evaporation. The resulting brown solid was slurried in 300 mL of 15% ethyl acetate/85% hexanes. The solid was collected by vacuum filtration yielding 35.1 grams of 2,3-dimethoxy-7,7-dimethyl-9-trifluoromethyl-7H-benzo[C]fluoren-5-ol. This material was not purified further but was used directly in the next step.

Step 6

The product from Step 6 (2,3-dimethoxy-7,7-dimethyl-9-trifluoromethyl-7H-benzo[C]fluoren-5-ol (8.8 grams), 1,1-bis(4-methoxyphenyl)-2-propyn-1-ol (7.9 grams) made in accordance to the procedure of Example 1, Step 1 of U.S. Pat. No. 5,458,814, which example is hereby specifically incorporated by reference herein, and dichloromethane (175 mL) were combined in a reaction flask. To this was added trifluoroacetic acid (260 mg) and p-toluenesulfonic acid (215 mg). The reaction mixture was stirred at room temperature for 5 hours and then washed with 50% saturated aqueous NaHCO$_3$ (200 mL). The organic layer was dried over anhydrous magnesium sulfate and concentrated by rotary evaporation. The resulting residue was purified by column chromatography on silica gel (450 grams) eluting with 15% hexanes/85% dichloromethane. Fractions containing product were combined and concentrated by rotary evaporation. The resulting solid was slurried in methanol and collected by vacuum filtration yielding 10.8 grams of a green solid. Mass Spectrometry and NMR analysis show the product to have a structure consistent with 3,3-di(4-methoxyphenyl)-6,7-dimethoxy-11-trifluoromethyl-13,13-dimethyl-3H,13H-indeno[2',3':3,4]naphtho[1,2-b]pyran as shown below.

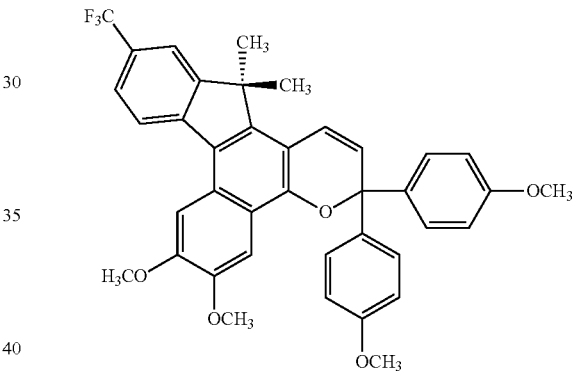

Example 2

Morpholine (1.4 mL) and anhydrous tetrahydrofuran (100 mL) were combined in a reaction flask. The reaction mixture was stirred at room temperature under a nitrogen atmosphere and a n-butyllithium solution (2.5M in hexanes, 6.2 mL) was added dropwise over 10 minutes. After stirring for 5 minutes, 3,3-di(4-methoxyphenyl)-6,7-dimethoxy-11-trifluoromethyl-13,13-dimethyl-3H,13H-indeno[2',3':3,4]naphtho[1,2-b]pyran from Example 1 Step 5 (5 g) was added to the reaction flask. The reaction mixture was stirred at room temperature for 2 hours. The reaction mixture was poured into a saturated aqueous sodium chloride solution and then acidified with concentrated hydrochloric acid until acidic. The layers were phase separated and the aqueous layer was extracted with one 100 mL portions of diethyl ether. The organic portions were combined and washed with saturated aqueous sodium chloride (200 mL). The organic layer was dried over anhydrous sodium sulfate and concentrated by rotary evaporation. The resulting brown solid was slurried in hot diethyl ether/hexane mixture (1:1), cooled to room temperature, collected by vacuum filtration and washed with cold diethyl ether/hexane mixture (1:1) yielding 4.8 grams of a white solid. Mass Spectrometry and NMR analysis show the product to have a structure consistent with 3,3-di(4-methoxyphenyl)-6-methoxy-7-morpholino-11-trifluoromethyl-13,13-dimethyl-3H,13H-indeno[2',3':3,4]naphtho[1,2-b]pyran as shown below.

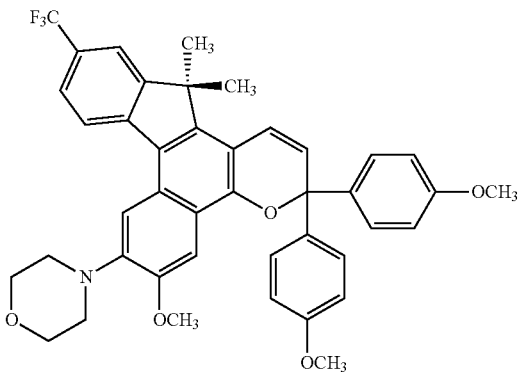

Comparative Example 1

The procedure of Example 1 was followed except that benzoyl chloride was used in place of 4-trifluoromethylbenzoyl chloride. Mass Spectrometry and NMR analysis show the product to have a structure consistent with 3,3-di(4-methoxyphenyl)-6,7-dimethoxy-13,13-dimethyl-3H,13H-indeno[2',3':3,4]naphtho[1,2-b]pyran Comparative Example 2

The procedure of Example 2 was followed except that Comparative Example 1 was used in place of Example 1. Mass Spectrometry and NMR analysis show the product to have a structure consistent with 3,3-di(4-methoxyphenyl)-6-methoxy-7-morpholino-13,13-dimethyl-3H,13H-indeno[2',3':3,4]naphtho[1,2-b]pyran.

Part 2: Photochromic Test Square Preparation

The photochromic performance of the photochromic materials of Examples 1-2 and Comparative Examples 1-2 were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a diamond blade saw into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max-vis}$ is the wavelength in the visible spectrum at which the maximum absorption of the activated-state form of the photochromic compound in a test square occurs. The $\lambda_{max-vis}$ wavelength was determined by testing the photochromic test squares in a Varian Cary 300 UV-Visible spectrophotometer; it may also be calculated from the spectrum obtained by the S2000 spectrometer on the optical bench.

The saturated optical density ("Sat'd OD") for each test square was determined by opening the shutter from the xenon lamp and measuring the transmittance after exposing the test chip to UV radiation for 30 minutes. The $\lambda_{max-vis}$ at the Sat'd OD was calculated from the activated data measured by the S2000 spectrometer on the optical bench. The First Fade Half Life ("$T_{1/2}$") is the time interval in seconds for the absorbance of the activated-state form of the photochromic material in the test squares to reach one half the Sat'd OD absorbance value at room temperature (73° F.), after removal of the source of activating light.

Part 3: Testing and Results

Results for the photochromic materials tested are listed below in Table 1.

TABLE 1

| Photochromic Test Data | | | |
| --- | --- | --- | --- |
| Example | $\lambda_{max}$ (nm) Visible | Sat. OD | Bleach $T_{1/2}$ (s) |
| 1 | 455 | 0.68 | 107 |
| CE 1 | 451 | 1.27 | 236 |
| 2 | 477 | 1.08 | 135 |
| CE2 | 471 | 1.68 | 337 |

These results show that the fade rate is significantly faster in the photochromic materials of the present invention versus each Comparative Example that does not have a substituent at the 11-position.

Whereas particular embodiments of this invention have been described above for purposes of illustration, it will be evident to those skilled in the art that numerous variations of the details of the present invention may be made without departing from the invention as defined in the appended claims.

We claim:

1. A photochromic material that is free of polymerizable unsaturated groups, said photochromic material represented by:

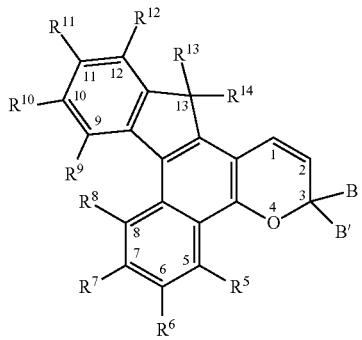

wherein:

B and B' are each independently:

a metallocenyl group;

an aryl group that is mono-substituted with a reactive substituent or a compatibilizing substituent;

9-julolidinyl, an unsubstituted, mono-, di- or tri-substituted aryl group chosen from phenyl and naphthyl, an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, wherein the aryl and heteroaromatic substituents are each independently:

hydroxy, aryl, mono- or di-$(C_1$-$C_{12})$alkoxyaryl, mono- or di-$(C_1$-$C_{12})$alkylaryl, $C_3$-$C_7$ cycloalkylaryl, $C_3$-$C_7$ cycloalkyl, $C_3$-$C_7$ cycloalkyloxy, $C_3$-$C_7$ cycloalkyloxy$(C_1$-$C_{12})$alkyl, $C_3$-$C_7$ cycloalkyloxy$(C_1$-$C_{12})$alkoxy, aryl$(C_1$-$C_{12})$alkyl, aryl$(C_1$-$C_{12})$alkoxy, aryloxy, aryloxy$(C_1$-$C_{12})$alkyl, aryloxy$(C_1$-$C_{12})$alkoxy, mono- or di-$(C_1$-$C_{12})$alkylaryl$(C_1$-$C_{12})$alkyl, mono- or di-$(C_1$-$C_{12})$alkoxyaryl$(C_1$-$C12)$alkyl, mono- or di-$(C_1$-$C_{12})$alkylaryl$(C_1$-$C_{12})$alkoxy, mono- or di-$(C_1$-$C_{12})$ alkoxyaryl $(C_1$-$C_{12})$alkoxy, amino, mono- or di-$(C_1$-$C_{12})$alkylamino, diarylamino, piperazino, N-$(C_1$-$C_{12})$ alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, mono$(C_1$-$C_{12})$ alkoxy$(C_1$-$C_{12})$alkyl, halogen or —C(=O)$R^{22}$, wherein $R^{22}$ is —O$R^{23}$, —N($R^{24}$) $R^{25}$, piperidino or morpholino, wherein $R^{23}$ is allyl, $C_1$-$C_6$ alkyl, phenyl, mono$(C_1$-$C_6)$alkyl substituted phenyl, mono$(C_1$-$C_6)$ alkoxy substituted phenyl, phenyl$(C_1$-$C_3)$alkyl, mono $(C_1$-$C_6)$alkyl substituted phenyl$(C_1$-$C_3)$alkyl, mono$(C_1$-$C_6)$alkoxy substituted phenyl $(C_1$-$C_3)$alkyl, $C_1$-$C_6$ alkoxy$(C_2$-$C_4)$ alkyl or $C_1$-$C_6$ haloalkyl, and $R^{24}$ and $R^{25}$ are each independently $C_1$-$C_6$ alkyl, $C_5$-$C_7$ cycloalkyl or a substituted or an unsubstituted phenyl, wherein said phenyl substituents are each independently $C_1$-$C_6$ alkyl or $C_1$-$C_6$ alkoxy;

an unsubstituted or mono-substituted group chosen from pyrazolyl, imidazolyl, pyrazolinyl, imidazolinyl, pyrrolidino, phenothiazinyl, phenoxazinyl, phenazinyl and acridinyl, said wherein said substituents are each independently $C_1$-$C_{12}$ alkyl, $C_1$-$C_{12}$ alkoxy, phenyl or halogen;

a 4-substituted phenyl, the substituent being a dicarboxylic acid residue, a diamine residue, an amino alcohol residue, a polyol residue, —(CH$_2$)—, —(CH$_2$)$_e$— or —[O—(CH$_2$)$_e$]f—, wherein e is an integer ranging from 2 to 6 and f is an integer ranging from 1 to 50, and wherein the substituent is connected to an aryl group of another photochromic material;

a group represented by:

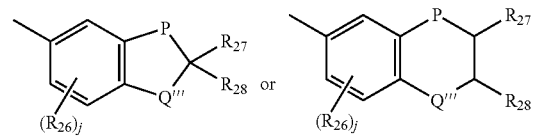

wherein P is —CH$_2$— or —O—; Q''' is —O— or substituted nitrogen, the substituted nitrogen substituents being hydrogen, $C_1$-$C_{12}$ alkyl or $C_1$-$C_{12}$ acyl, provided that when Q''' is substituted nitrogen, P is —CH$_2$—; each $R^{26}$ is independently $C_1$-$C_{12}$ alkyl, $C_1$-$C_{12}$ alkoxy, hydroxy or halogen; $R^{27}$ and $R^{28}$ are each independently hydrogen or $C_1$-$C_{12}$ alkyl; and j is an integer ranging from 0 to 2;

$R^5$, $R^8$, $R^9$ and $R^{12}$ are each independently:

hydrogen, $C_1$-$C_6$ alkyl, chloro, fluoro, bromo, $C_3$-$C_7$ cycloalkyl or a unsubstituted, mono- or di-substituted phenyl, wherein said phenyl substituents are each independently $C_1$-$C_6$ alkyl or $C_1$-$C_6$ alkoxy;

—O$R^{40}$ or —OC(=O)$R^{40}$, wherein $R^{40}$ is hydrogen, amine, alkylene glycol, polyalkylene glycol, $C_1$-$C_6$ alkyl, phenyl$(C_1$-$C_3)$alkyl, mono$(C_1$-$C_6)$alkyl substituted phenyl$(C_1$-$C_3)$alkyl, mono$(C_1$-$C_6)$alkoxy substituted phenyl$(C_1$-$C_3)$alkyl, $(C_1$-$C_6)$alkoxy$(C_2$-$C_4)$alkyl, $C_3$-$C_7$ cycloalkyl, mono$(C_1$-$C_4)$alkyl substituted $C_3$-$C_7$ cycloalkyl or an unsubstituted, mono- or di-substituted phenyl, wherein said phenyl substituents are each independently $C_1$-$C_6$ alkyl or $C_1$-$C_6$ alkoxy;

a 4-substituted phenyl, the substituent being a dicarboxylic acid residue, a diamine residue, an amino alcohol residue, a polyol residue, —(CH$_2$)—, —(CH$_2$)$_e$— or —[O—(CH$_2$)$_e$]f—, wherein e is an integer ranging from 2 to 6, and f is an integer ranging from 1 to 50, and wherein the substituent is connected to another photochromic material;

—N($R^{41}$)$R^{42}$, wherein $R^{41}$ and $R^{42}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_8$ cycloalkyl, $C_4$-$C_{16}$ bicycloalkyl, $C_5$-$C_{20}$ tricycloalkyl or $C_1$-$C_{20}$ alkoxy$(C_1$-$C_6)$alkyl, or $R^{41}$ and $R^{42}$ come together with the nitrogen atom to form a $C_3$-$C_{20}$ hetero-bicycloalkyl ring or a $C_4$-$C_{20}$ hetero-tricycloalkyl ring;

a nitrogen containing ring represented by:

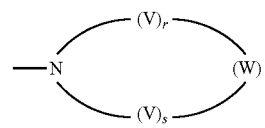

wherein each —V— is independently chosen for each occurrence from —CH$_2$—, —CH($R^{43}$)—, —C($R^{43}$)$_2$—, —CH(aryl)-, —C(aryl)$_2$- and —C($R^{43}$)(aryl)-, wherein each $R^{43}$ is independently $C_1$-$C_6$ alkyl and each aryl is independently phenyl or naphthyl; —W— is —V—, —O—, —S—, —S(O)—, —SO$_2$—, —NH—, —N($R^{43}$)— or —N(aryl)-; s is an integer ranging from 1 to 3; and r is an integer ranging from 0 to 3, provided that if r is 0, then —W— is the same as —V; or a group represented by:

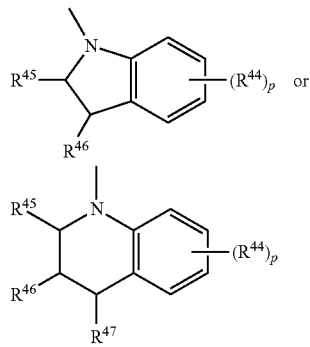

wherein each $R^{44}$ is independently $C_1$-$C_6$ alkyl, $C_1$-$C_6$ alkoxy, fluoro or chloro; $R^{45}$, $R^{46}$ and $R^{47}$ are each independently hydrogen, $C_1$-$C_6$ alkyl, phenyl or naphthyl, or $R^{45}$ and $R^{46}$ together form a ring of 5 to 8 carbon atoms, and p is an integer ranging from 0 to 3;

$R^6$ and $R^7$ are each independently a moderate to strong electron-donating group selected from:

(i) the group —$OR^{8'}$, wherein $R^{8'}$ is phenyl($C_1$-$C_3$)alkyl, $C_1$-$C_6$ alkyl, mono($C_1$-$C_6$)alkyl substituted phenyl ($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or $R^{8'}$ is the group, —CH($R^{9'}$)Q''', wherein $R^{9'}$ is hydrogen or $C_1$-$C_3$ alkyl and Q''' is —CN, —COOH, —COOCH$_3$, or —COOCH$_2$CH$_3$;

(ii) —N(R15)R16, wherein R15 and R16 each independently comprises hydrogen, C1-C8 alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, C1-C8 alkylaryl, C3-C20 cycloalkyl, C4-C20 bicycloalkyl, C5-C20 tricycloalkyl and C1-C20 alkoxyalkyl, wherein said aryl group is phenyl or naphthyl;

(iii) a nitrogen containing ring represented by the following graphic formula:

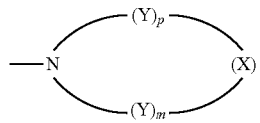

wherein Y is selected from the group consisting of —CH2—, —CH(R17)-, —C(R17)(R17)-, —CH(aryl)-, —C(aryl)2-, and —C(R17)(aryl)-, and X is selected from the group consisting of —Y—, —O—, —S—, —S(O)—, —S(O2)-, —NH—, —NR17- and —N-aryl, wherein R17 is C1-C6 alkyl, said aryl substituent is phenyl or naphthyl, m is the integer 1, 2 or 3, and p is the integer 0, 1, 2, or 3, provided that when p is 0, X is Y; or (iv) a group represented by one of the following graphic formulae:

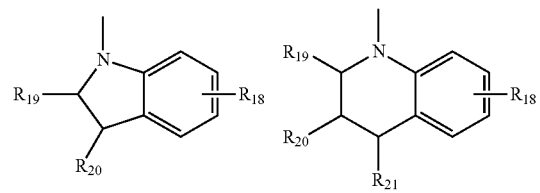

wherein $R_{19}$, $R_{20}$ and $R_{21}$ are each hydrogen, $C_1$-$C_5$ alkyl, phenyl or naphthyl, or the groups $R_{19}$ and $R_{20}$ may come together to form a ring of 5 to 8 carbon atoms; and $R_{18}$ is $C_1$-$C_6$ alkyl, $C_1$-$C_6$ alkoxy, fluoro or chloro;

$R^{10}$ is any of the groups of $R^5$, $R^8$, $R^9$ and $R^{12}$ or a metallocenyl group;

$R^{11}$ is an is an α-haloalkyl, α,α-dihaloalkyl, trihalomethyl group, a perhalo($C_2$-$C_{10}$)alkyl group, a perhaloalkoxy group, or the group —O—C(O)—R, wherein R is a linear or branched group chosen from $C_1$-$C_{10}$ alkyl, $C_1$-$C_{10}$ haloalkyl, or $C_1$-$C_{10}$ perhaloalkyl;

$R^{13}$ and $R^{14}$ do not form a spirocyclic group and are each independently a ($C_1$-$C_6$)alkyl group, a ($C_1$-$C_6$)alkoxy group, a hydroxy($C_1$-$C_6$)alkyl or the polyalkoxylated group T represented by the formula:

wherein —Z is —C(O)— or —CH$_2$— and Z' is hydroxy, epoxy or $C_1$-$C_3$ alkoxy and letters x, y and z are each an integer between 0 and 50 and the sum of x, y and z is an integer between 2 and 50.

2. The photochromic material of claim 1, wherein each of $R^{13}$ and $R^{14}$ independently is a ($C_1$ to $C_6$) alkyl group or a ($C_1$ to $C_6$) alkoxy group.

* * * * *